United States Patent
Nekich et al.

(10) Patent No.: US 8,382,706 B2
(45) Date of Patent: Feb. 26, 2013

(54) USER INTERFACE FOR CONFIGURING AN INVASIVE CARDIOLOGY DIGITAL SIGNAL AMPLIFIER AND METHOD OF USE

(75) Inventors: Nicholas Paul Nekich, New Berlin, WI (US); Patrick Thomas Moran, New Berlin, WI (US); Daniel Richard Schneidewend, Monomonee Falls, WI (US); Linda Marie Helvick, Colgate, WI (US); David Allen Powell, Saukville, WI (US)

(73) Assignee: General Electric Company, Schenectady, NY (US)

( * ) Notice: Subject to any disclaimer, the term of this patent is extended or adjusted under 35 U.S.C. 154(b) by 1719 days.

(21) Appl. No.: 11/735,322

(22) Filed: Apr. 13, 2007

(65) Prior Publication Data

US 2008/0255504 A1    Oct. 16, 2008

(51) Int. Cl.
*A61M 31/00* (2006.01)
(52) U.S. Cl. .................................... 604/95.01
(58) Field of Classification Search .................. 434/262; 623/901; 700/95–98; 703/13; 604/523, 604/264, 95.01
See application file for complete search history.

(56) References Cited

U.S. PATENT DOCUMENTS

| | | | | |
|---|---|---|---|---|
| 7,371,067 B2* | 5/2008 | Anderson et al. | ............. | 434/262 |
| 7,769,427 B2* | 8/2010 | Shachar | ........................ | 600/424 |
| 7,812,815 B2* | 10/2010 | Banerjee et al. | ............. | 345/156 |

* cited by examiner

*Primary Examiner* — Manuel Mendez
(74) *Attorney, Agent, or Firm* — McAndrews, Held & Malloy, Ltd.; William Kryger

(57) ABSTRACT

Certain embodiments of the present invention provide systems and methods for catheter input management. Certain embodiments provide a user interface system facilitating catheter monitoring. The system includes a virtual catheter input module (CIM) corresponding to and representing a physical CIM that is adapted to be connected to at least one catheter. The system also includes a configuration module establishing a catheter configuration for the virtual CIM based on a plurality of configuration settings for a catheter channel. At least one catheter channel is assigned to a virtual input port on the virtual CIM. The configuration module applies the catheter configuration for at least one catheter channel when a catheter is connected to a physical input port on the physical CIM corresponding to the virtual input port on the virtual CIM.

20 Claims, 8 Drawing Sheets

FIG. 7

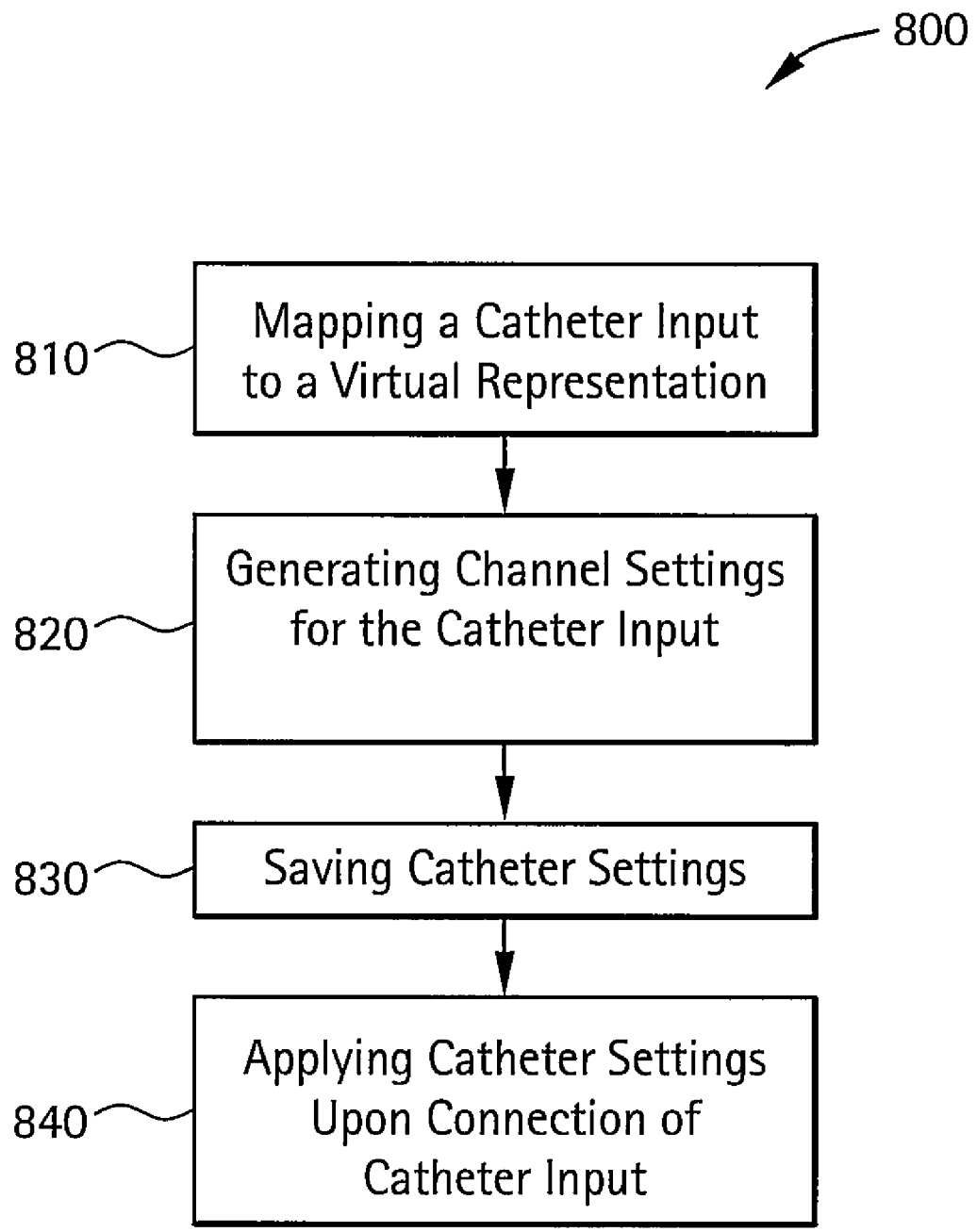

USER INTERFACE FOR CONFIGURING AN INVASIVE CARDIOLOGY DIGITAL SIGNAL AMPLIFIER AND METHOD OF USE

BACKGROUND OF THE INVENTION

The present invention generally relates to catheter input monitoring and configuration. In particular, the present invention relates to systems and methods for virtual catheter input module management.

The normal pumping of the heart results from the ordered contraction of the muscles of the heart, the myocardium. When the myocardium is electrically stimulated, it contracts. The sinoatrial node (SA node) generates an electrical impulse that is propagated to the myocardium. Typically, the SA node spontaneously generates the electrical impulse. Certain problems may occur when the electrical impulse is generated and/or propagates incorrectly.

An electrophysiology (EP) study may include one or more tests performed to acquire data about the electrical signals in the heart. An EP study is performed by placing one or more catheters into a patient's heart. The catheters monitor the electrical signals in the heart. A catheter may include one or more leads for relaying the monitored signals to a catheter monitoring system such as an EP laboratory system. In some situations, a catheter may be used to stimulate the heart by introducing electrical impulses in an EP study.

An intracardiac (IC) channel is an electrical trace between two electrodes located within the heart. The electrodes are located on a catheter, which is placed into the heart. Selecting two poles from the catheter(s) and then displaying the resulting signal create the intracardiac channel. Intracardiac channels can be created in the following manner: Any two poles from a single catheter (bipolar channel), any single pole from the catheter and a reference point (unipolar channel), or by using a single pole from two different catheters (cross-catheter bipolar channel). There are many properties of this signal that can be enhanced to improve the usefulness of the signal, such as: Gain, High Pass Filters, Low Pass Filters and Notch Filters.

For example, to perform an EP study, three intracardiac (IC) catheters may be placed into a patient's heart to monitor the electrical signals as they travel through the heart and cross the three catheters. A cardiac amplifier may be used to amplify received catheter input. The cardiac amplifier includes several components, including a Catheter Input Module (CIM). The catheters may be connected to input ports on a catheter input module (CIM) that is part of the monitoring system. The CIM physically connects the catheter connectors to the cardiac amplifier hardware. Each catheter may have one or more data channels. A data channel includes a signal electrode and a reference electrode. The reference electrode may come from a lead in the catheter or from an auxiliary or external reference, for example.

For cardiac diagnosis, a physician looks for clear, clean cardiograms. An acquisition system should capture electrophysiological signals as small as 1 mV. The signals should be captured with very little noise and displayed, stored and sent to other equipment in a real-time or substantially real-time manner. The signals should be filtered in a variety of ways, and the captured data should reject artifacts caused by other equipment such as pace makers and ablation devices. Therefore, an invasive cardiology digital signal amplifier may be used to amplify acquired signal data with reduced noise.

Current systems utilize an amplifier to receive and amplify input from IC catheters. The number of inputs available for the IC catheters may be fixed based on the amplifier model purchased. Thus, when additional catheter inputs are desired, a user must currently replace the entire amplifier with a different model, incurring additional cost and system downtime. In other current systems, the amplifier may utilize one or more CIMs. In such systems, when additional catheter inputs are desired, the catheter monitoring system must be powered down and opened up for the new CIM hardware to be installed.

As discussed above, current systems do not support the addition of additional catheter inputs to the hardware during a study. However, the number of catheter inputs needed during a study can change. For example, during a study a healthcare practitioner may determine an additional catheter is desired to be included in the study. As another example, at the beginning of a study, only a subset of the leads from a catheter may be used. During the study, the healthcare provider may decide to utilize additional leads. If additional catheter inputs are not available when desired during the study, the study will have to be closed before the amplifier can be replaced or powered down so additional CIMs can be added.

In some systems, a study configuration may be used. A study configuration is a set of saved intracardiac channel settings, including but not limited to, channel labels, pole configurations, filtering options, etc. Additionally, the study configuration may contain other settings that pertain to a specific type of procedure that do not relate directly to the intracardiac catheters, but do pertain to the type of study being performed, for example. A study configuration allows an end user to more quickly retrieve pre-configured settings based on the type of case being performed. It would be desirable to allow a user to make a change to an existing study configuration and make the changed information available to save, load and edit for future cases.

Typically, when a clinical study is in progress and there is a change in direction of the case, the user may need to change the current catheter configuration. A change in catheter configuration involves disconnection and connection of many wires as well as creation of new intracardiac channels to support the new catheter in use. Currently, no method allows a user to connect a catheter to a CIM and dynamically create pre-defined intracardiac channels based on the type of catheter being connected.

Additionally, if several catheters are in use during a study, determining which catheters are currently connected to a CIM may be challenging, especially since the amplifier is typically installed near the patient table, and the software and configuration is located in a separate control room. A system and/or method providing a virtual or software depiction of CIM configuration to a user would be highly desirable.

Furthermore, a system and/or method for adding additional intracardiac channels to a given study would be highly desirable. There is a need for an interface allowing a user to create a new bipolar, unipolar or cross catheter bipolar channel. An interface allowing a user to define label, gain and filter settings for a new intracardiac display channel would be highly desirable.

Furthermore, a user interface allowing a software application to properly display the cardiograms captured by the amplifier would be highly desirable.

BRIEF SUMMARY OF THE INVENTION

Certain embodiments of the present invention provide systems and methods for catheter input management. Certain embodiments provide a user interface system facilitating catheter monitoring. The system includes a virtual catheter input module (CIM) corresponding to and representing a physical CIM that is adapted to be connected to at least one catheter. The system also includes a configuration module establishing a catheter configuration for the virtual CIM based on a plurality of configuration settings for a catheter channel. At least one catheter channel is assigned to a virtual input port on the virtual CIM. The configuration module applies the catheter configuration for at least one catheter channel when a catheter is connected to a physical input port on the physical CIM corresponding to the virtual input port on the virtual CIM.

Certain embodiments provide a method for catheter input module management. The method includes mapping a virtual CIM to a physical CIM. The method also includes assigning a catheter channel to at least one virtual port of the virtual CIM. The method further includes generating a catheter configuration for the at least one virtual port of the virtual CIM based on a plurality of catheter configuration settings.

Certain embodiments provide a computer readable medium having a set of instructions for execution on a computing device. The set of instructions includes a user interface routine accepting user input relating at least catheter configuration and displaying output relating to at least catheter configuration. The set of instructions also includes a virtual CIM corresponding to and representing a physical CIM that is adapted to be connected to at least one catheter. Further, the set of instructions includes a configuration routine establishing a catheter configuration for the virtual CIM based on a plurality of configuration settings for a catheter channel. At least one catheter channel is assigned to a virtual input port on the virtual CIM. The configuration routine applies the catheter configuration for at least one catheter channel when a catheter is connected to a physical input port on the physical CIM corresponding to the virtual input port on the virtual CIM.

BRIEF DESCRIPTION OF SEVERAL VIEWS OF THE DRAWINGS

FIG. 7 illustrates an exemplary user interface screen demonstrating configuration of several virtual catheter input module ports in accordance with an embodiment of the present invention.

FIG. 8 illustrates a flow diagram for method for virtual catheter input module management according to an embodiment of the present invention.

Figure 1:
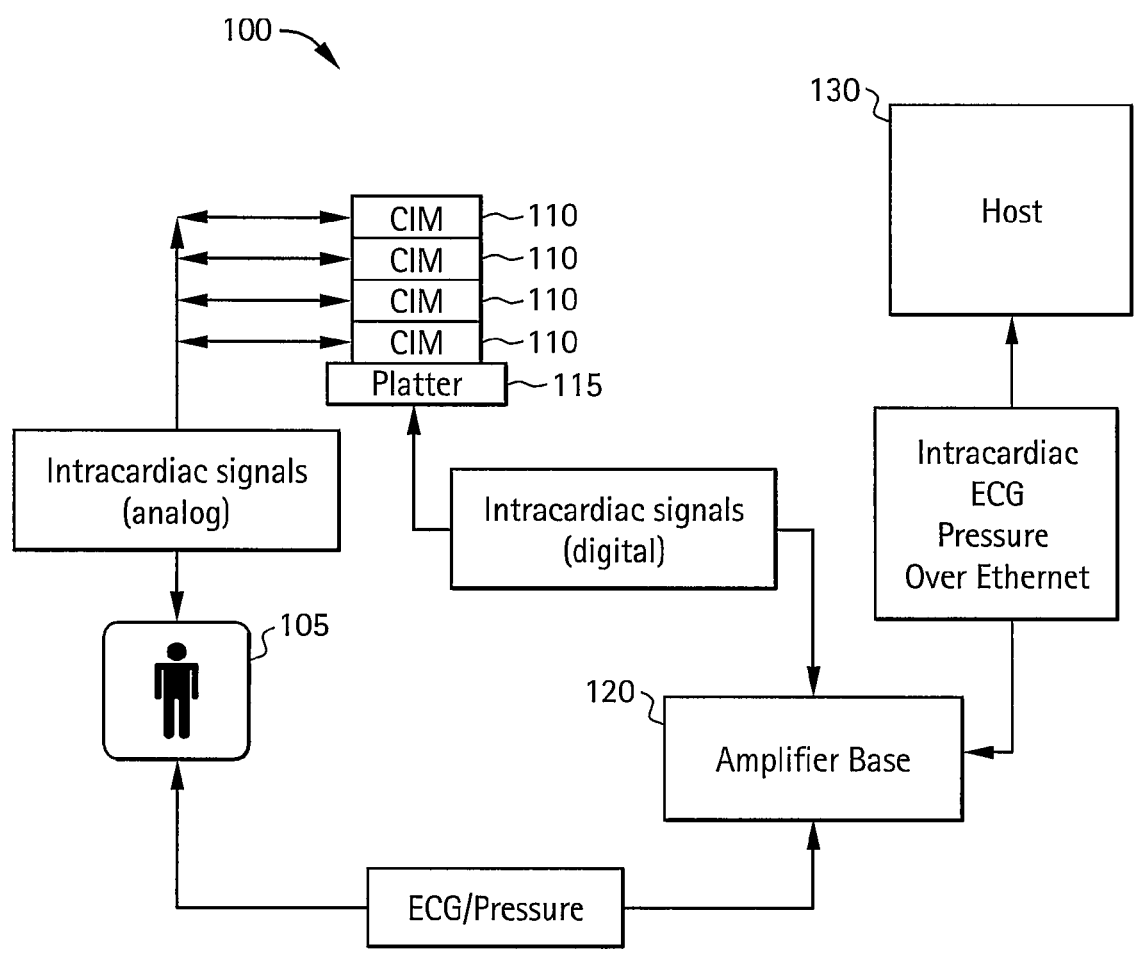
FIG. 1 illustrates a catheter monitoring system according to an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a catheter monitoring system 100 according to an embodiment of the present invention. The catheter monitoring system 100 includes one or more catheter input modules (CIMs) 110, an amplifier base 120, and a host 130. The CIMs 110 are in communication with the amplifier base 120. The amplifier base 120 is in communication with the host 130. In certain embodiments, the CIMs 110 may be coupled to the amplifier base 120 through a platter 115.

In operation, one or more catheters are inserted into a patient 105. The catheters may be intracardiac (IC) catheters, for example. The catheters may be placed into various locations in the heart of the patient 105, for example. For example, catheters may be inserted as part of an EP study.

A catheter sends signal data to the amplifier base 120 through one or more CIMs 110. The catheters may include one or more electrodes with leads connecting to input ports on a CIM 110, for example. The leads may connect to a socket, plug, and/or one or more pins of a catheter input port, for example.

Each catheter may have one or more data channels. A data channel includes a signal electrode and a reference electrode. The reference electrode may come from a lead in the catheter or from an auxiliary or external reference, for example. Multiple channels may share a reference electrode. For example, an electrode from the catheter may serve as a reference for several other leads to form multiple channels. As another example, an external reference signal, such as a surface electrode, may be utilized as the reference for one or more channels.

A CIM 110 receives the signal data from a catheter through a catheter port in the CIM 110. For example, one or more leads from the catheter may be plugged into the catheter port in the CIM 110. The catheter port may include a socket, plug, and/or one or more pins, for example.

The CIM 110 communicates the signal data from the catheter to the amplifier base 120 through a data port in the CIM 110. For example, the data port of the CIM may be connected to the amplifier base 120 by a cable. In certain embodiments, the cable may be daisy-chained with other CIMs 110. In certain embodiments, a cable may be directly connected from each CIM 110 to the amplifier base 120.

As mentioned above, in certain embodiments, a CIM 110 is connected to the amplifier base 120 through a platter 115. For example, a cable may be connected to the data port of a first CIM 110, daisy-chained to the data port of a second CIM 110, and then connected to a platter 115. The platter 115 may then include a connection such as a cable to the amplifier base 120. In certain embodiments, the platter 115 is part of the amplifier base 120.

The amplifier base 120 is adapted to receive data from one or more CIMs 110. The amplifier base 120, as described above, may receive the data from the one or more CIMs 110 through the platter 115, for example.

The amplifier base 120 may receive data from inputs other than the CIMs 110. For example, the amplifier base 120 may receive data from a surface lead. As another example, the amplifier base 120 may receive data from a blood pressure monitor.

The amplifier base 120 may amplify or process the received data. For example, the amplifier base 120 may increase the gain on the signal data from a CIM 110. As another example, the amplifier base 120 may filter noise from the signal data from a CIM 110.

After receiving the data, and any processing, the amplifier base 120 communicates the data to the host 130. The amplifier base 120 may communicate the received data as a digital signal. Alternatively, the amplifier base 120 may communicate the received data as an analog signal. The amplifier base 120 may communicate the data to the host 130 over a wired and/or wireless connection, for example. For example, the amplifier base 120 may communicate the data to the host 130 using the Ethernet protocol. As another example, the amplifier base 120 may communicate the data to the host 130 using a special-purpose communication protocol. The special-purpose protocol may include slots for some predetermined number of data sources. Each slot may include data from the source or a value indicating the source is not present or the data is not valid, for example.

The host 130 receives data from the amplifier base 120. The host 130 is adapted to present the data. The host may display the data to a user, for example. The host 130 is adapted to save the data. The host may save the data to a file or an information management system, for example.

The host 130 may display and/or save the data based on a configuration, for example. The configuration may be user-defined. For example, the configuration may indicate that data from a particular catheter, signal, or channel is to be displayed at a certain location on the screen or in a certain color. As another example, the configuration may indicate that a filter is to be applied to the data.

A user may make a configuration for signals that are not currently being received. For example, a user may provide configurations for 18 channels, while only 8 are in use. When a new channel is added, the host will then utilize the appropriate configuration for that new channel. When no data is received for a channel, the channel may not be displayed. When data starts being received at the host 130 for the channel, the channel may then be displayed and processed based at least in part on the configuration.

The host 130 may process received data. The data may be processed before it is presented and/or saved, for example. As mentioned above, the host 130 may process received data based at least in part on a configuration. For example, the host 130 may apply a low pass filter to the data. The low pass filter may have a range from 100 to 1000 Hz, for example. As another example, the host 130 may apply a high pass filter to the data. The high pass filter may have a range from 0.05 to 30 Hz, for example. The type of filtering and the ranges may be configured by a user, for example.

As discussed above, it is desirable to add new CIMs 110 to the catheter monitoring system 100 during a study. Certain embodiments of the present invention include hot-swappable CIMs 110, for example. That is, the CIM 110 is adapted to be connected during a study, without powering down the system 100. In other words, the CIM 110 is adapted to be connected when the system 100 is powered on. For example, the CIM 110 may be connected to the amplifier base 120 during the study. As another example, the CIM 110 may be connected to the platter 115 during the study. In certain embodiments of the present invention, the CIM 110 is adapted to be connected to the system 100 during the normal operating mode of the system 100. That is, the system 100 does not need to be powered down or placed into a suspended mode for the CIM 110 to be connected or disconnected.

In addition, according to certain embodiments of the present invention, a CIM 110 may be removed from the system 100 during a study. The CIM 110 may be disconnected from the amplifier base 120 during a study. The CIM 110 may be disconnected without powering down the system 100 and/or the amplifier base 120. The CIM 110 may be disconnected during the normal operating mode of the system 100.

In certain embodiments, the circuits of the CIM 110 are protected against excessive current draw. In certain embodiments, 12 Volt input power of the CIM 110 is protected with a 1 Amp rated PolySwitch resettable over-current protection device, such as a Raychem SMD 110. In certain embodiments, the +5 Volt and +3.3 Volt internal power supplies of the CIM 110 are protected with a 3 Amp rated non-latching output over-current protection built into the power modules. For example, a Tyco AXA003A0X-5RZ may be utilized.

In certain embodiments, the circuits of the CIM 110 are protected against electrostatic discharge. In certain embodiments, +12 Volt input power, +5 Volt and +3.3 Volt internal power supplies are protected from over-voltage with transient suppressor diodes. For example, On Semiconductor 1SMB13AT3 and/or On Semiconductor 1SMB5.0AT3 may be used. In certain embodiments, analog signals are protected from over-voltage with switching diodes such as National Electronics MMBD1503A, connected to +5 Volt and ground power rails. In certain embodiments, RS-485 digital communication signals are protected by RS-485 digital transceivers, such as Texas Instruments 75HVD10D, which have built-in electrostatic discharge and short circuit protection.

In certain embodiments, the portion of the data port of the CIM 110 that communicates data signals may be physically offset from the portion of the data port of the CIM 110 that provides power to the CIM 110. Thus, in the normal action of using the port, the signal connections may be made before the power connections. This may prevent damage to the hardware of the CIM 110 and/or the system 100 during connection and/or disconnection of the CIM 110.

The amplifier base 120 is adapted to detect the connection of a new CIM 110 during a study. The amplifier base 120 may detect the connection of the CIM 110 by the availability of data, for example. As another example, the amplifier base 120 may detect the connection of the CIM 110 based at least in part on the flow of power. The amplifier base 120 is adapted to configure the new CIM 110 when it is connected. The amplifier base 120 is adapted to communicate data received from the new CIM 110 to the host 130.

As discussed above, the host 130 is adapted to process the new data received during a study. For example, the host 130 may display the new data when it is received based at least in part on a user-defined configuration. As another example, the host 130 may begin filtering the data channels received from the new CIM 110. As another example, the host 130 may begin saving the new data received from the CIM 110 when it is connected during a study.

Figure 2:
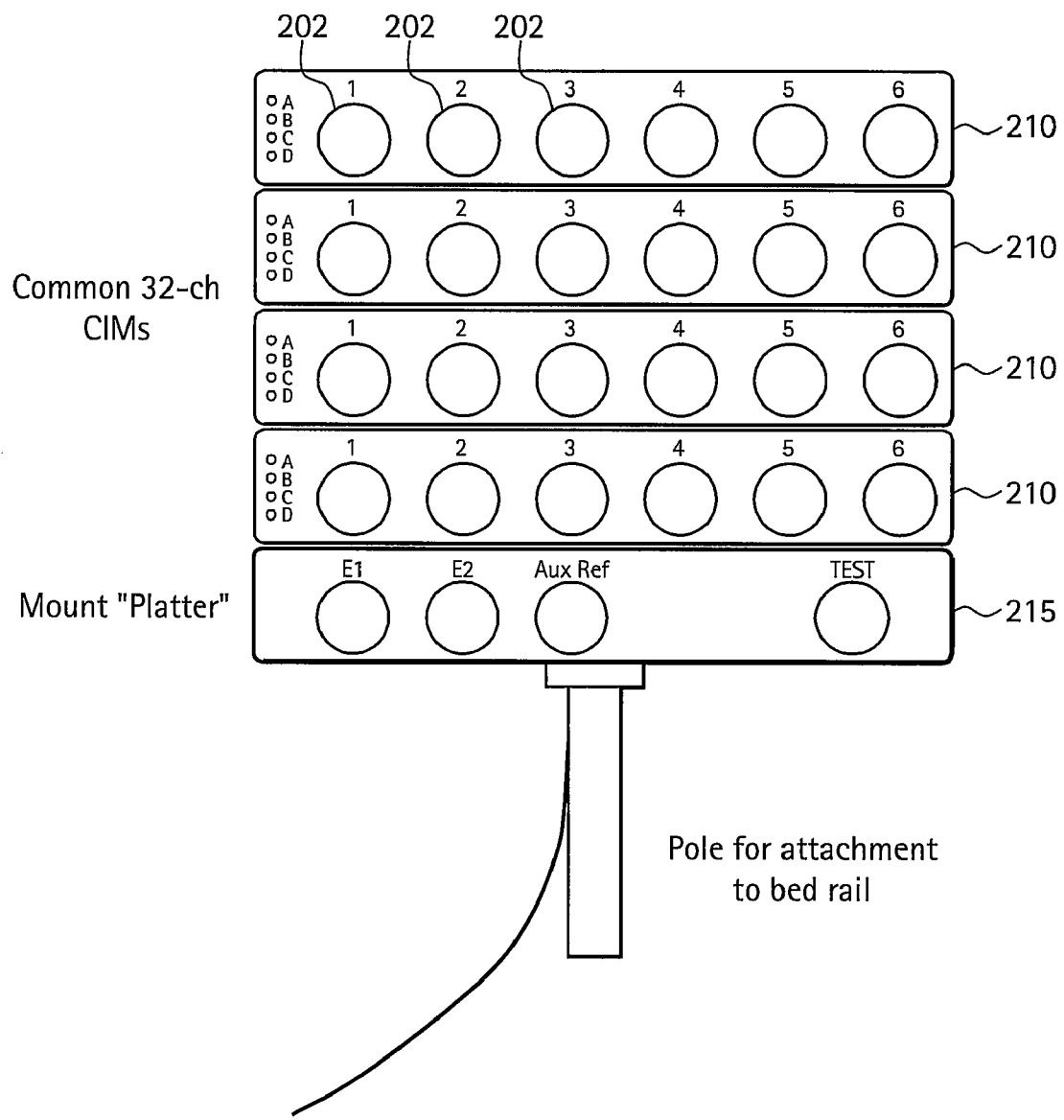
FIG. 2 illustrates a front view of four catheter input modules and a platter according to an embodiment of the present invention.

FIG. 2 illustrates a front view of four catheter input modules 210 and a platter 215 according to an embodiment of the present invention. The catheter input modules 210 may be similar to the CIMs 110, described above, for example. The platter 215 may be similar to the platter 115, described above, for example.

Each CIM 210 includes one or more catheter ports 202. As discussed above, a CIM 210 may receive signal data from a catheter through a catheter port 202. For example, one or more leads from the catheter may be plugged into the catheter port 202 in one or more CIMs 210. The catheter port 202 may include a socket, plug, and/or one or more pins, for example.

In certain embodiments, the CIM 210 includes an indicator. The indicator may include a light, light-emitting diode (LED), and/or liquid crystal display (LCD), for example. The indicator may identify the CIM 210 to a user when the CIM 210 is connected to the catheter monitoring system. For example, a light may be illuminated when the CIM 210 is connected and configured by the catheter monitoring system during a study.

Figure 3:
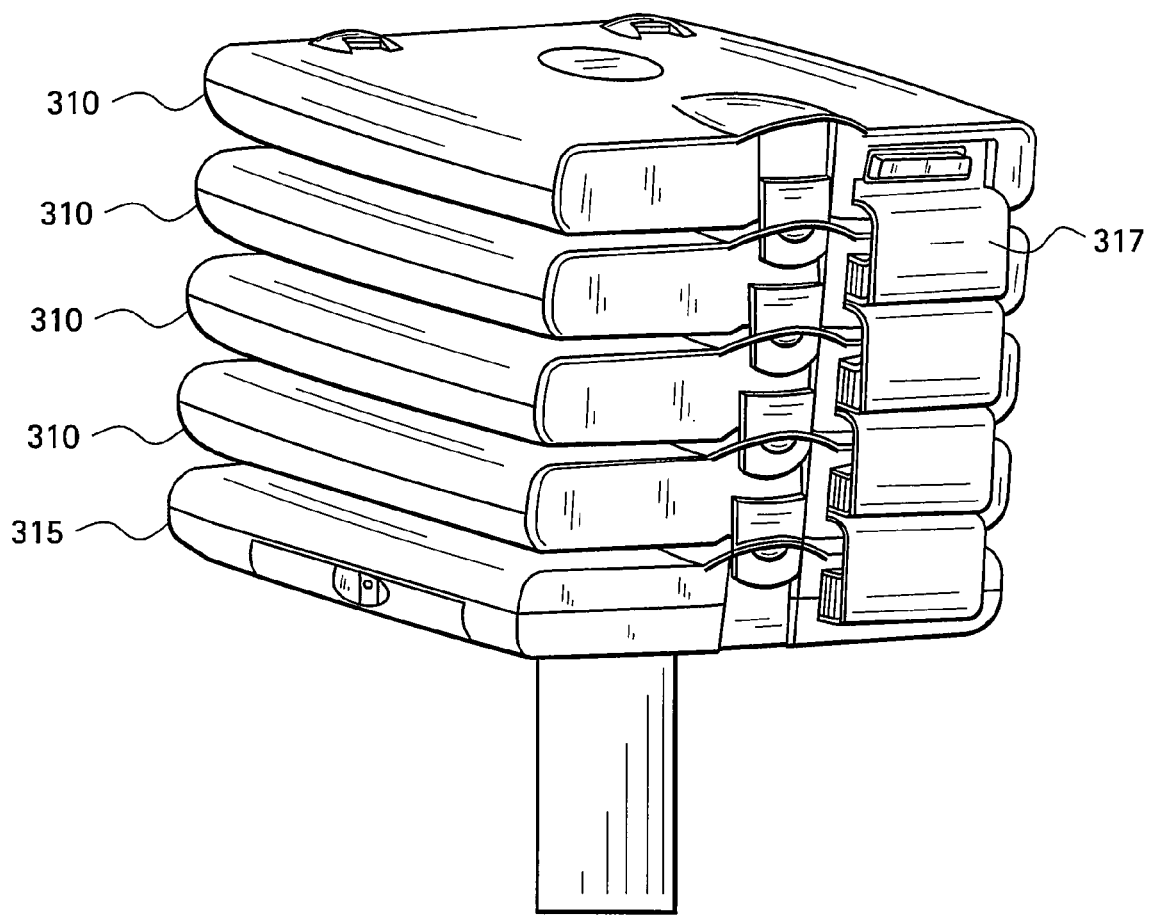
FIG. 3 illustrates a rear perspective view of four catheter input modules and a platter according to an embodiment of the present invention.

FIG. 3 illustrates a rear perspective view of four catheter input modules 310 and a platter 315 according to an embodiment of the present invention. The catheter input modules 310 may be similar to the CIMs 110 and/or the CIMs 210, described above, for example. The platter 315 may be similar to the platter 115 and/or the platter 215, described above, for example.

As illustrated in FIG. 3, a cable 317 is daisy-chained to each of the CIMs 310 in a manner similar to that described above. The cable 317 is connected to the data port of each CIM 310. In addition, the cable 317 connects the CIMs 310 to the platter 315. A data port may include a socket, plug, and/or one or more pins, for example.

The cable 317 communicates data between a CIM 310 and a catheter monitoring system. The catheter monitoring system may be similar to the catheter monitoring system 100, described above, for example. The cable 317 communicates the data from a CIM 310 through the platter 315.

The components, elements, and/or functionality of catheter monitoring system 100, as well as the components illustrated in FIGS. 2 and 3 and described above, may be implemented alone or in combination in various forms in hardware, firmware, and/or as a set of instructions in software, for example. Certain embodiments may be provided as a set of instructions residing on a computer-readable medium, such as a memory or hard disk, for execution on a general purpose computer or other processing device, such as, for example, a PACS workstation or one or more dedicated processors.

Figure 4:
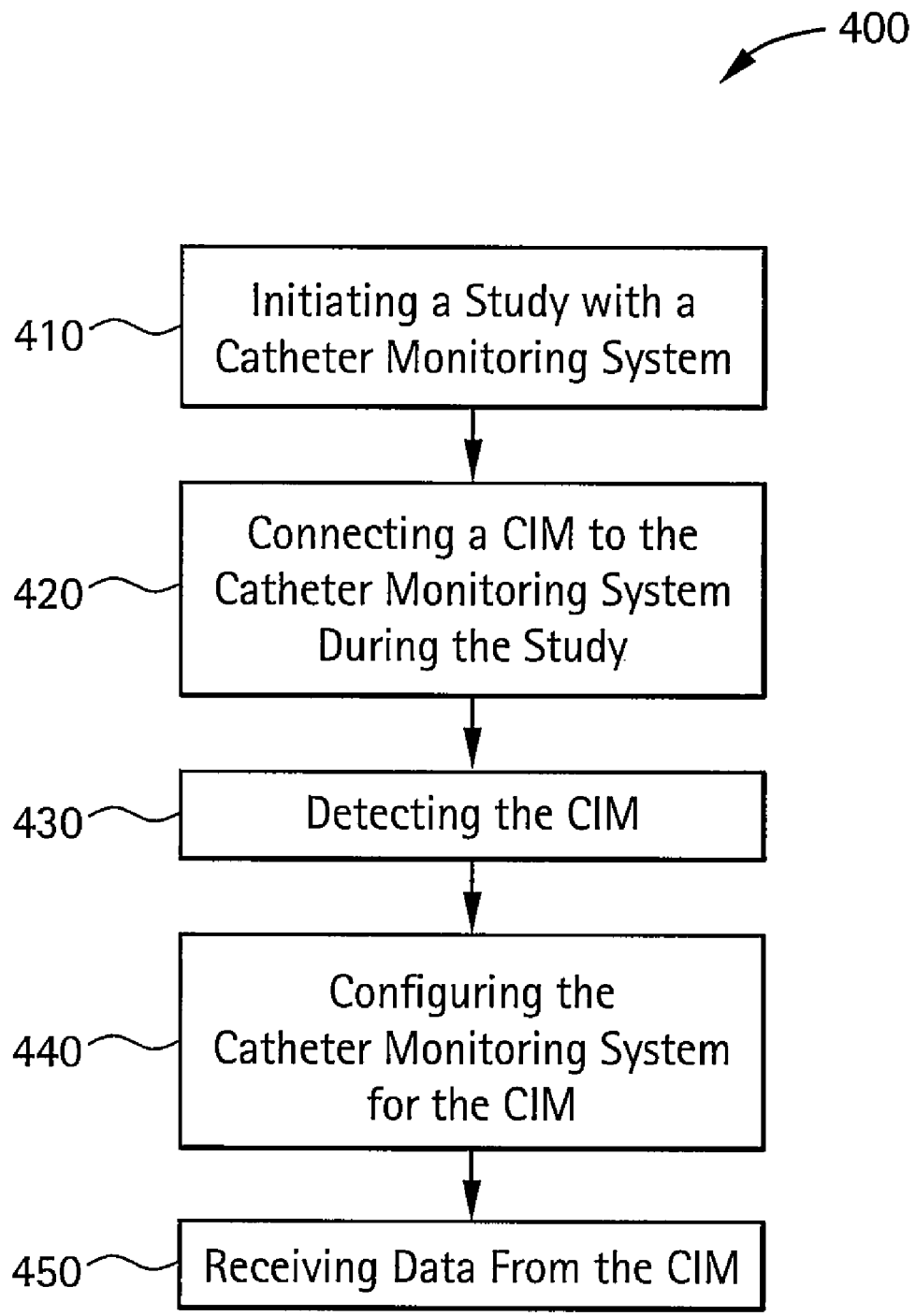
FIG. 4 illustrates a flow diagram for a method for medical navigation according to an embodiment of the present invention.

FIG. 4 illustrates a flow diagram for a method 400 for medical navigation according to an embodiment of the present invention. The method 400 includes the following steps, which will be described below in more detail. At step 410, a study is initiated with a catheter monitoring system. At step 420, a catheter input module (CIM) is connected to the catheter monitoring system during the study. At step 430, the CIM is detected. At step 440, the catheter monitoring system is configured for the CIM. At step 450, data is received from the CIM. The method 400 is described with reference to elements of systems described above, but it should be understood that other implementations are possible.

At step 410, a study is initiated with a catheter monitoring system. The catheter monitoring system may be similar to the catheter monitoring system 100, described above, for example. The study may be an EP study, for example.

At step 420, a catheter input module (CIM) is connected to the catheter monitoring system during the study. The catheter input module may be similar to the CIM 110, 210, and/or 310, described above, for example. The study may be the study initiated at step 410, described above, for example.

The CIM may be a hot-swappable CIM, for example. That is, the CIM may be adapted to be connected during a study, without powering down the system. In other words, the CIM may be adapted to be connected when the system is powered on. For example, the CIM 110 may be connected to the amplifier base 120 during the study. As another example, the CIM 110 may be connected to the platter 115 during the study. In certain embodiments of the present invention, the CIM is adapted to connect to the system during the normal operating mode of the system. That is, the system does not need to be powered down or placed into a suspended mode for the CIM to be connected or disconnected.

In addition, according to certain embodiments of the present invention, the CIM may be removed from the system during a study. The CIM 110 may be disconnected from the amplifier base 120 during a study, for example. The CIM 110 may be disconnected without powering down the system 100 and/or the amplifier base 120, for example.

In certain embodiments, the circuits of the CIM are protected against excessive current draw. In certain embodiments, the circuits of the CIM are protected against electrostatic discharge. In certain embodiments, the portion of the data port of the CIM that communicates data signals may be offset from the portion of the data port of the CIM that provides power to the CIM. Thus, the signal connections may be made before the power connections.

At step 430, the CIM is detected. The CIM may be the CIM connected at step 420, described above, for example. The CIM may be detected by the catheter monitoring system, for example. The CIM may be detected by an amplifier base similar to the amplifier base 120, described above, for example.

The catheter monitoring system may detect the CIM by the presence of data at a port of the catheter monitoring system, for example. As another example, the catheter monitoring system may detect the connection of the CIM based at least in part on the flow of power.

At step 440, the catheter monitoring system is configured for the CIM. The catheter monitoring system may be configured based at least in part on a user-defined configuration for the CIM, for example. For example, when the new CIM is detected, the catheter monitoring system may begin processing, storing, and/or displaying the data from the new CIM. The processing, storing, and/or displaying of the data may be performed by the host of the catheter monitoring system. The host may be similar to the host 130, described above, for example. The catheter monitoring system may filter the received data, for example. As another example, the catheter monitoring system may display the received data in accordance with a configuration.

At step 450, data is received from the CIM. The data may be received at the amplifier base of the catheter monitoring system. The amplifier base may be similar to the amplifier base 120, described above, for example. The data may be received at the host of the catheter monitoring system. The host may be similar to the host 130, described above, for example.

One or more of the steps of the method 400 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

In certain embodiments, a user interface may be used with a catheter monitoring system, such as the system 100, to allow a user to create virtual catheters that are assigned to a virtual CIM when configuring a catheter monitoring system. A virtual catheter has an associated name, description and a set of default channels based on a number of poles assigned to the catheter, for example. The channel settings can be edited by a user and then saved as default channels for the specific virtual catheter. The user may also edit an existing catheter configuration to facilitate change to the default channels to that catheter.

In certain embodiments, the user interface allows the user to visually correlate physical catheter inputs with logical software catheter inputs on screen. The user is able to select a virtual input and assign a pre-defined catheter to this input. Assigning a catheter to a virtual CIM port may automatically generate settings to display intracardiac signals (as defined by the user for the catheter defaults). Once a catheter is assigned to a virtual input, a user may configure a catheter label name, gain settings, filter settings, and any other settings associated with the selected channel. The interface allow the user to input a catheter into the CIM, assign it to the virtual CIM input, and automatically create channels based on user preferences, for example. In certain embodiments, if a particular catheter involves more than one physical CIM input, the user interface automatically allows a catheter to span multiple virtual inputs.

A user may create a pre-defined set of information (e.g., a study configuration) that corresponds to a hardware configuration. The information/catheter configuration in the study configuration can be re-configured to accommodate additional CIM modules, such as by moving catheters from one input to another, adding catheter(s) to inputs, and/or removing catheter(s) from inputs.

A user may create intracardiac channels that are not defined in default catheter settings. Channel creation may include channels generated within the scope of a single catheter or across different catheters, for example. These channels may include an ability to be configured as bipolar, unipolar or cross-catheter bipolar channels. The number of available channels is based on the number of poles associated with a catheter, for example.

Once channels have been defined for a specific configuration, the user can save these settings. Saving a configuration allows the user to load settings (e.g., channels/catheter configuration) when performing a case using the same equipment configuration. Additionally, the user may edit a saved configuration in the event that equipment, process, or the case warrants a change to the saved configuration.

The user interface may allow a user to clear an existing catheter from one of the virtual software inputs if the user changes the physical catheter that is currently connected. This should result in any associated channels being removed from the configuration.

The user interface may allow the user to change the current intracardiac waveform settings. These settings include, but are not limited to: filter settings, gain settings, label information and waveform color. The user will have the option to save these changes to either the study in progress or to the default study configuration for this type of case.

The user interface allows the user to manually add or remove intracardiac channels from the study configuration. This includes bipolar, unipolar or cross catheter bipolar channels.

Figure 5:
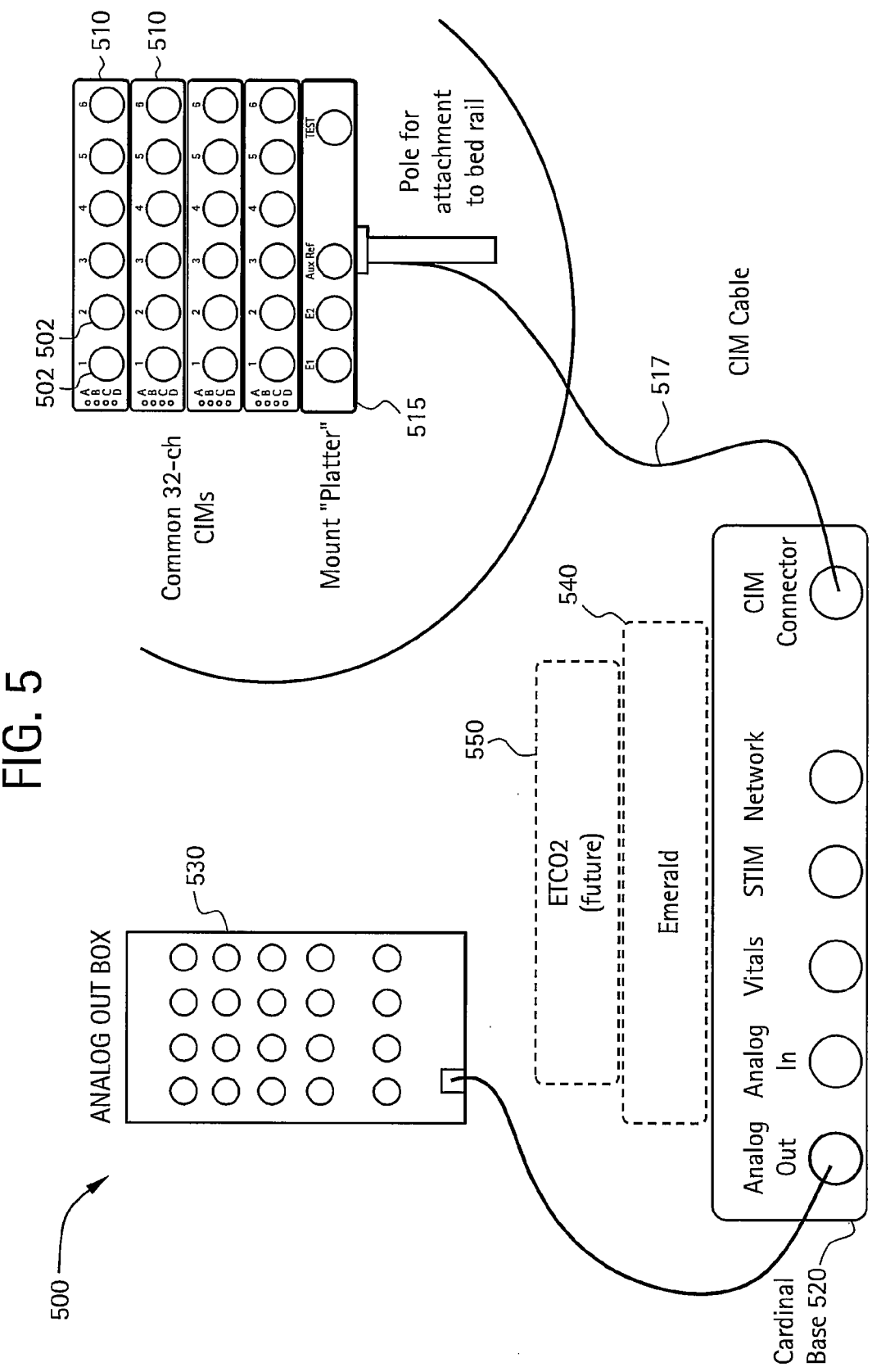
FIG. 5 illustrates exemplary catheter monitoring system physical hardware configured by a user interface according to an embodiment of the present invention.

FIG. 5 illustrates exemplary physical catheter monitoring system hardware 500 configured by a user interface according to an embodiment of the present invention. The system 500 shown in FIG. 5 includes one or more catheter input modules (CIMs) 510, a platter 515, an amplifier base 520, and an analog output 530. The CIMs 510 include one or more ports 502. The CIMs 510 are in communication with the amplifier base 520. The amplifier base 520 is in communication with the analog output 530. In certain embodiments, the CIMs 510 may be coupled to the amplifier base 520 through a platter 515. In certain embodiments, the amplifier base 520 may also be connected to a patient monitoring and interface system 540 and/or a measurement system 550, for example. In certain embodiments, the system 500 may function similarly to the system 100 described above.

A catheter sends signal data to the amplifier base 520 through one or more CIMs 510. The catheters may include one or more electrodes with leads connecting to input ports 502 on a CIM 510, for example. The leads may connect to a socket, plug, and/or one or more pins of a catheter input port 502, for example.

Each catheter may have one or more data channels. A data channel includes a signal electrode and a reference electrode. The reference electrode may come from a lead in the catheter or from an auxiliary or external reference, for example. Multiple channels may share a reference electrode. For example, an electrode from the catheter may serve as a reference for several other leads to form multiple channels. As another example, an external reference signal, such as a surface electrode, may be utilized as the reference for one or more channels.

A CIM 510 receives the signal data from a catheter through a catheter port 502 in the CIM 510. For example, one or more leads from the catheter may be plugged into the catheter port 502 in the CIM 510. The catheter port 502 may include a socket, plug, and/or one or more pins, for example.

The CIM 510 communicates the signal data from the catheter to the amplifier base 520 through a data port in the CIM 510. For example, the data port of the CIM 510 may be connected to the amplifier base 520 by a cable 517. In certain embodiments, the cable 517 may be daisy-chained with other CIMs 510, for example. In certain embodiments, a cable 517 may be directly connected from each CIM 510 to the amplifier base 520.

As mentioned above, in certain embodiments, a CIM 510 is connected to the amplifier base 520 through a platter 515. For example, a cable 517 may be connected to the data port of a first CIM 510, daisy-chained to the data port of a second CIM 510, and then connected to a platter 515. The platter 515 may then include a connection such as a cable 517 to the amplifier base 520. In certain embodiments, the platter 515 is part of the amplifier base 520.

The amplifier base 520 is adapted to receive data from one or more CIMs 510. The amplifier base 520, as described above, may receive the data from the one or more CIMs 510 through the platter 515, for example.

The amplifier base 520 may receive data from inputs other than the CIMs 510. For example, the amplifier base 520 may receive data from a surface lead. As another example, the amplifier base 520 may receive data from a blood pressure monitor and/or other vital sign monitor. The amplifier base 520 may also generate stimulator output (STIM) for a patient. The amplifier base 520 may amplify or process the received data. For example, the amplifier base 520 may increase the gain on the signal data from a CIM 510. As another example, the amplifier base 520 may filter noise from the signal data from a CIM 510. The amplifier base 520 may communicate data as analog and/or digital data, for example.

In certain embodiments, the amplifier base 520 may be connected to one or more additional components, such as a measurement device 550 and/or a patient monitoring and interface device 540. The measurement device 550 may measure patient data such as an end-tidal carbon dioxide concentration in expired air (ETCO2) measurement. The monitoring device 540 may monitor patient vitals and/or other data, interface with clinical information systems, etc.

As described above, a user may configure CIM channels, add and/or remove CIMs 510, etc., in the system 500.

The components, elements, and/or functionality of catheter monitoring system 500 may be implemented alone or in combination in various forms in hardware, firmware, and/or as a set of instructions in software, for example. Certain embodiments may be provided as a set of instructions residing on a computer-readable medium, such as a memory or hard disk, for execution on a general purpose computer or other processing device, such as, for example, a PACS workstation or one or more dedicated processors.

Figure 6:
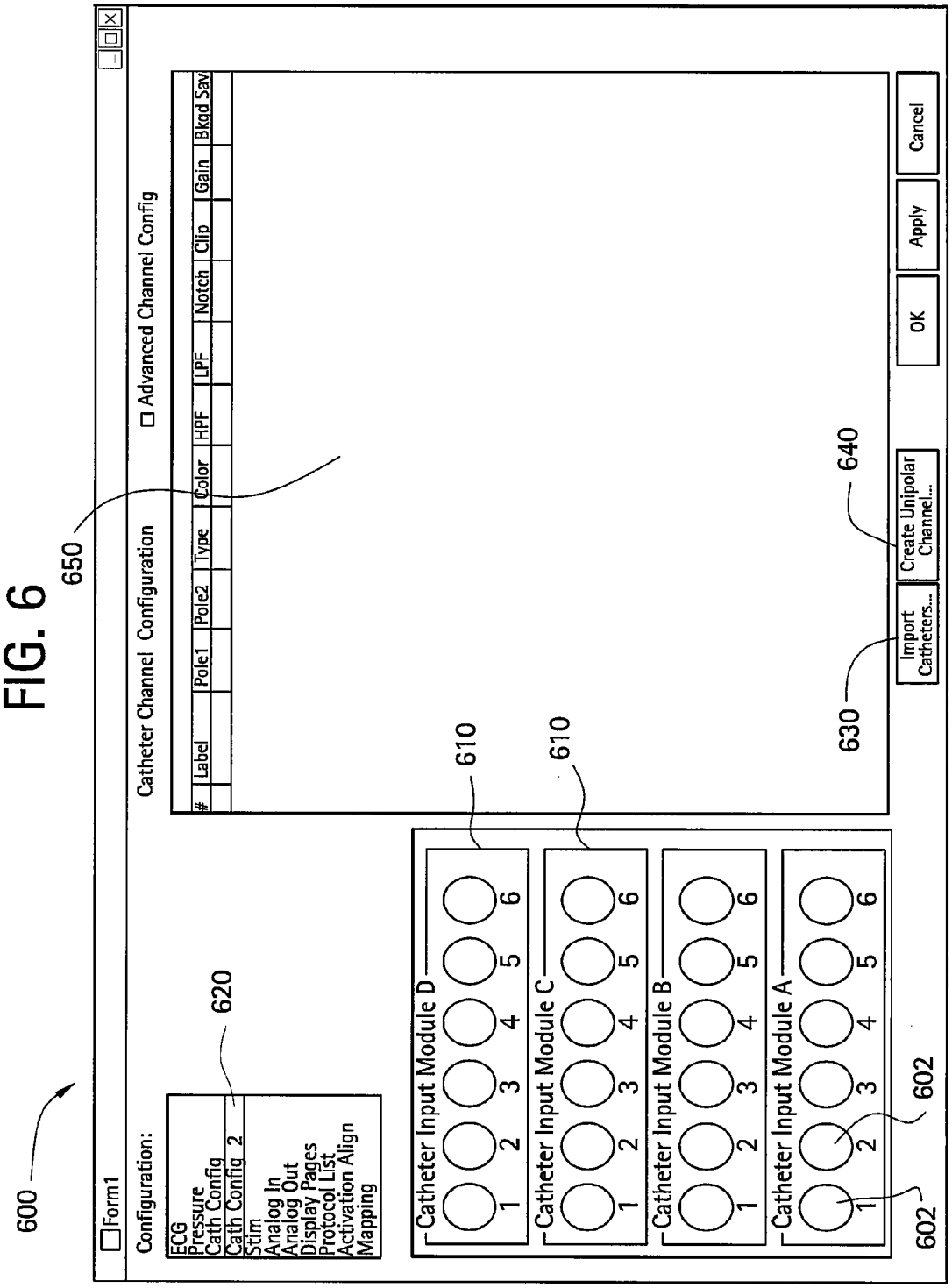
FIG. 6 illustrates an exemplary user interface screen displaying a blank configuration in accordance with an embodiment of the present invention.

FIG. 6 illustrates an exemplary user interface screen 600 displaying a blank configuration in accordance with an embodiment of the present invention. In FIG. 6, no catheters have been configured using the interface 600. As shown in FIG. 6, the interface 600 includes virtual representations of catheter input modules (CIMs) 610, as well as ports 602 within the CIMS 610. The interface 600 allows a user to select from a variety of configuration options 620. Via the interface 600, for example, a user may configure ECG data, blood pressure measurement, patient stimulation, analog inputs, analog outputs, display settings, protocol options, mappings, activation alignments, catheter channel configurations, etc. The interface 600 may include one or more additional features allowing a user to import other catheter configurations 630, create unipolar channel settings 640, etc. For a catheter channel, a user may configure settings such as one or more poles, catheter type, color setting, high pass filter setting, low pass filter, notch setting, clip percentage, gain setting, saving enabled/disabled, etc. A user may assign a label to such a channel configuration 650 and save configuration information. Configuration information may be later retrieved, automatically applied upon connection of a catheter, edited, deleted, etc.

Figure 7:
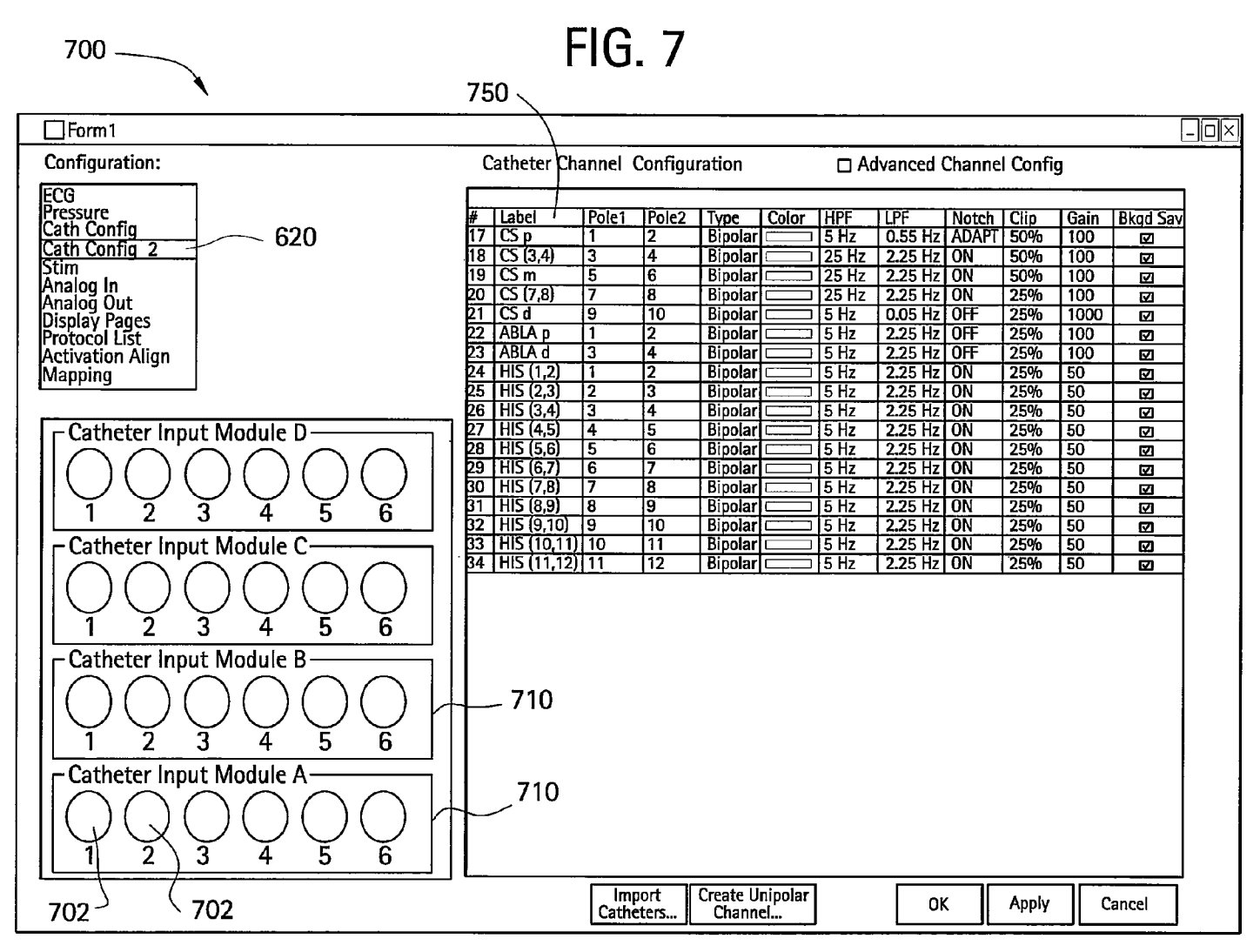

FIG. 7 illustrates an exemplary user interface screen 700 demonstrating configuration of several virtual CIM ports in accordance with an embodiment of the present invention. The interface 700 shows the interface 600 described above with channel configuration information for several CIM ports 702. For Catheter Input Module A 710, the interface 700 shows four ports 702 configured for 1) a Coronary Sinus (CS) catheter, 2) an ablation (ABLA) catheter, 3) a first His catheter and 4) a second His catheter. For each port 702, several labels have been created for different catheter channel configurations 750. A user may add to the configurations 750, edit one or more configurations 750, delete one or more configurations 750, etc., via the user interface 700. When a physical catheter is connected to a physical CIM 110, saved configuration information 750 for a corresponding virtual CIM 710 may be selected and/or automatically applied for that CIM 110, for example.

FIG. 8 illustrates a flow diagram for method 800 for virtual catheter input module management according to an embodiment of the present invention. At step 810, a catheter input is mapped to a virtual input representation. For example, a physical catheter input is correlated with a logical or virtual software representation of a catheter input and displayed for a user.

At step 820, channel settings are generated for the catheter input. For example, default settings may be generated automatically and/or by manual trigger for the input. Alternatively and/or in addition, one or more settings may be prescribed by a user for the catheter input channel. Settings may govern intracardiac and/or other signal input, display, processing, output and/or other user preference, for example. At step 830, catheter settings are saved. Settings may be later modified, deleted, etc., automatically and/or by a user.

At step 840, settings are applied upon connection of a catheter to the catheter input. Settings may be applied automatically upon detection of the catheter input, for example. Settings may be applied upon selection by the user, for example. In certain embodiments, a user may modify one or more settings on application to a catheter input. Catheter input is received and displayed, processed, saved, relayed, etc.

One or more of the steps of the method 800 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Thus, certain embodiments provide a user interface having the look and feel of physical catheter input monitoring hardware. If the hardware changes, the same action can be performed on the virtual CIM to configure the intracardiac display channels, for example.

Certain embodiments provide a user interface that allows configuration to be based on the types of catheters being connected to the monitoring hardware. Catheter-based configuration may be used to more closely match actual clinical workflow, for example.

In certain embodiments, assigning a set of default channels to a specific catheter helps to increase configuration speed. In certain embodiments, configuration of catheter inputs and a cardiac amplifier is based on assigning a pre-defined catheter with default channel configurations to a virtual CIM input port. If no changes to defaults are to be made, then configuring a catheter for an input port involves reduced interaction from an end user. One or more intracardiac channels may be added and/or removed, for example, by adding or removing pre-defined catheters from a virtual CIM. Certain embodiments provide a technical effect of such virtual configuration.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A user interface system facilitating catheter monitoring, said system comprising:
   a virtual catheter input module (CIM) corresponding to and representing a physical CIM that is adapted to be connected to at least one catheter; and
   a configuration module establishing a catheter configuration for said virtual CIM based on a plurality of configuration settings for a catheter channel, at least one said catheter channel assigned to a virtual input port on said virtual CIM, said configuration module applying said catheter configuration for at least one said catheter channel when a catheter is connected to a physical input port on said physical CIM corresponding to said virtual input port on said virtual CIM.

2. The system of claim 1, wherein said configuration module is adapted to detect a connection of a catheter to said physical CIM, and wherein said configuration module is adapted to configure said CIM based on said catheter configuration when said connection is detected.

3. The system of claim 1, wherein said configuration module allows a user to define a configuration for a CIM when the CIM is not connected to be used when the CIM is connected.

4. The system of claim 1, wherein said configuration module provides a default configuration for at least one said catheter channel.

5. The system of claim 1, wherein said configuration module allows a user to at least one of create, modify and delete at least one catheter configuration for at least one virtual input port on at least one virtual CIM.

6. The system of claim 1, wherein said catheter configuration spans a plurality of virtual input ports on a virtual CIM.

7. The system of claim 1, wherein said plurality of configuration settings comprises one or more of catheter label name, gain, filter, poles, type, waveform color, notch and clip.

8. The system of claim 1, wherein said configuration module assigns a predefined catheter with automatically generated default channel configurations to a virtual CIM.

9. The system of claim 1, wherein said catheter channel spans multiple CIMs.

10. The system of claim 1, wherein said virtual CIM mirrors an appearance of said physical CIM.

11. A method for catheter input module management, said method comprising:
  mapping a virtual catheter input module (CIM) to a physical CIM;
  assigning a catheter channel to at least one virtual port of said virtual CIM; and
  generating a catheter configuration for said at least one virtual port of said virtual CIM based on a plurality of catheter configuration settings.

12. The method of claim 11, further including detecting the connection of a CIM and applying said catheter configuration to said virtual CIM and said physical CIM upon detection.

13. The method of claim 11, further comprising providing a default configuration for said catheter channel.

14. The method of claim 11, further comprising allowing a user to at least one of create, modify and delete at least one catheter configuration for at least one virtual input port on at least one virtual CIM.

15. The method of claim 11, further comprising assigning a predefined catheter with automatically generated default channel configurations to a virtual CIM.

16. The method of claim 11, further comprising saving said catheter configuration.

17. The method of claim 11, wherein said catheter configuration spans a plurality of virtual input ports on a virtual CIM.

18. The method of claim 11, wherein said plurality of configuration settings comprises one or more of catheter label name, gain, filter, poles, type, waveform color, notch and clip.

19. The method of claim 11, wherein said catheter channel spans multiple CIMs.

20. A computer readable medium having a set of instructions for execution on a computing device, said set of instructions comprising:
  a user interface routine accepting user input relating at least catheter configuration and displaying output relating to at least catheter configuration;
  a virtual catheter input module (CIM) corresponding to and representing a physical CIM that is adapted to be connected to at least one catheter; and
  a configuration routine establishing a catheter configuration for said virtual CIM based on a plurality of configuration settings for a catheter channel, at least one said catheter channel assigned to a virtual input port on said virtual CIM, said configuration routine applying said catheter configuration for at least one said catheter channel when a catheter is connected to a physical input port on said physical CIM corresponding to said virtual input port on said virtual CIM.

* * * * *